US008809816B2

(12) United States Patent
Komrakov (10) Patent No.: US 8,809,816 B2
(45) Date of Patent: Aug. 19, 2014

(54) MULTIPURPOSE DEVICE FOR TRANSMITTING RADIATION FROM A SOURCE TO AN OBJECT

(71) Applicant: Evgeny Vyacheslavovich Komrakov, Sankt-Peterburg (RU)

(72) Inventor: Evgeny Vyacheslavovich Komrakov, Sankt-Peterburg (RU)

(73) Assignee: Quantrill Estate Inc. (VG)

( * ) Notice: Subject to any disclaimer, the term of this patent is extended or adjusted under 35 U.S.C. 154(b) by 0 days.

(21) Appl. No.: 13/628,569

(22) Filed: Sep. 27, 2012

(65) Prior Publication Data

US 2013/0306882 A1    Nov. 21, 2013

(30) Foreign Application Priority Data

May 15, 2012   (RU) ................................ 2012119833

(51) Int. Cl.
*G21K 5/04*   (2006.01)
(52) U.S. Cl.
USPC ................. 250/494.1; 250/492.1; 250/504 R
(58) Field of Classification Search
USPC ................ 250/453.11, 455.11, 492.1, 493.1, 250/494.1, 504 R
See application file for complete search history.

(56) References Cited

U.S. PATENT DOCUMENTS

2008/0237489 A1* 10/2008 Hirono ....................... 250/492.1

FOREIGN PATENT DOCUMENTS

| RU | 2177452 | 12/2001 |
| RU | 2009133146 | 9/2009 |
| WO | 2011028147 | 10/2011 |

* cited by examiner

*Primary Examiner* — Nicole Ippolito
(74) *Attorney, Agent, or Firm* — Paul & Paul (57) ABSTRACT

A multipurpose device for transmitting radiation from a source to an object comprises two antennas, each designed as a truncated segment of a spherical or cylindrical surface, a radiation source provided in the aperture plane of one of the antennas, and an object placed in the combined focal area of the two antennas. The antennas are positioned opposite one another at a distance of from 0.6 to double the radius of the spherical or cylindrical surface, and the radiation source is of a distributed type. The antenna design effectively concentrates radiation emitted by a distributed source on an object placed in the focal area of the antenna, providing greater efficiency of radiation transmission, the possibility of radiation power variation, a more uniform concentration of radiation, an increase in the volume of the focal area without replacing the radiation source, increased reliability of the system, and reduced power requirements.

7 Claims, 8 Drawing Sheets

MULTIPURPOSE DEVICE FOR TRANSMITTING RADIATION FROM A SOURCE TO AN OBJECT

FIELD OF THE INVENTION

The invention relates to an reflector design and may be used for effectively concentrating radiation emitted by a distributed source on an object placed in the focal area of the reflector.

BACKGROUND OF THE INVENTION

The last few decades have been a period of transition from powerful single ultrahigh frequency (UHF) radiation sources such as magnetrons, klystrons, traveling wave lamps, and so on to distributed radiation sources consisting of a plurality of single solid-state elements. Similar developments occur with lamps in the light and ultraviolet ranges as well. Powerful single lamps are increasingly replaced with distributed light-emitting diode systems. It is common knowledge that a plurality of single solid-state UHF elements or light-emitting diodes improves the reliability and economic efficiency of the systems many times over. This invention can be used with a high effect specifically for concentrating radiation emitted by such and any other distributed radiation systems consisting of single elements.

A variety of inventions are used in prior art to transmit radiation from a source to an object. In particular, a prior art device for treating liquids with ultraviolet radiation disclosed in Russian Patent RU 2,177,452, published on Dec. 27, 2001, comprises a hollow outer cylindrical shell provided with orifices at the base thereof and an inlet and outlet pipes connected thereto, and a hollow inner cylindrical shell provided with stiffening ribs and arranged coaxially with the outer shell; ultraviolet lamps placed in housings of a material transparent to ultraviolet radiation in the annular gap between the shells parallel to the generatrices thereof and inserted into the orifices at the base of the outer shell, and flux generating means. The lamps are spaced in the annular gap along concentric circles, the inlet and outlet pipes are coaxial with the shells, and the flux generating means are provided on the directrixes of the inner shall on the outer side thereof. The prior art device is difficult to manufacture technologically and, therefore, has a high prime cost; besides, the lamps used in it have a low economic efficiency and reliability.

The closest related prior art of this invention is a device for transmitting radiation from a source to an object that is disclosed in Russian Application RU 2009133146 published on Mar. 10, 2011. The device comprises a radiation source placed in a shielded chamber together with object positioning means and two reflectors designed as truncated segments of a spherical surface and placed opposite one another at a distance equal to the radius of the spherical surface, the object positioning means being placed in the combined focal area of both reflectors, and the radiation source being provided in the aperture plane of either of the reflectors.

The device is disadvantageous because radiation is transmitted from the source to the object with an insufficient efficiency, radiation is concentrated extremely unevenly, the combined focal area is not large enough, and the radiation power cannot be varied unless the radiation source itself is replaced.

SUMMARY OF THE INVENTION

The technical result achieved by the use of the claimed invention consists in greater efficiency of radiation transmission from a source to an object, the possibility of radiation power variation, a more uniform concentration of radiation, a significant increase in the volume of the focal area without replacing the radiation source itself, increased reliability of the system, and reduced power requirements.

The claimed technical result is achieved in a multipurpose device for transmitting radiation from a source to an object comprising two reflectors, each designed as a truncated segment of a curved surface and both arranged to produce a combined focal area; a distributed source of radiation provided in the aperture plane of at least one of the reflectors or in one of the focal areas of each reflector, and an object placed in the combined focal area of the two reflectors. The curved surface of each reflector may be a spherical or cylindrical surface, and the distributed source of radiation is provided in the aperture plane of at least one of the reflectors. The reflectors may be arranged opposite, or at an angle to, one another to produce a combined focal area.

This technical result is also achieved by further providing the multipurpose device with at least an additional pair of spherical or cylindrical reflectors in a plane normal to the plane of the first pair of reflectors.

Furthermore, the curved surface of the reflectors may be formed by at least a pair of elliptical cylinders arranged opposite one another to produce a combined focal area for an object to be placed therein, with distributed sources placed in the two other focal areas. One elliptical reflector only is used in at least two planes and the distributed source is provided in the focal area of each reflector, the object being placed in the combined focal area of these reflectors.

The reflectors designed each as a truncated segment of a curved surface and arranged to produce a combined focal area increase significantly the concentration of radiation in the focal area and, accordingly, enhance the efficiency of radiation transmission from a source to an object.

A device provided with at least a further pair of spherical or cylindrical reflectors in a plane normal to the plane of the first pair of reflectors is capable of varying the radiation power and making concentration of the radiation more uniform by expanding significantly the volume of the focal area without replacing the radiation source itself.

The distributed radiation sources enhance the reliability of the system and reduce power requirements.

BRIEF DESCRIPTION OF THE DRAWINGS

The claimed invention is illustrated in the accompanying drawings wherein:

DESCRIPTION OF THE PREFERRED EMBODIMENT

Figure 1:
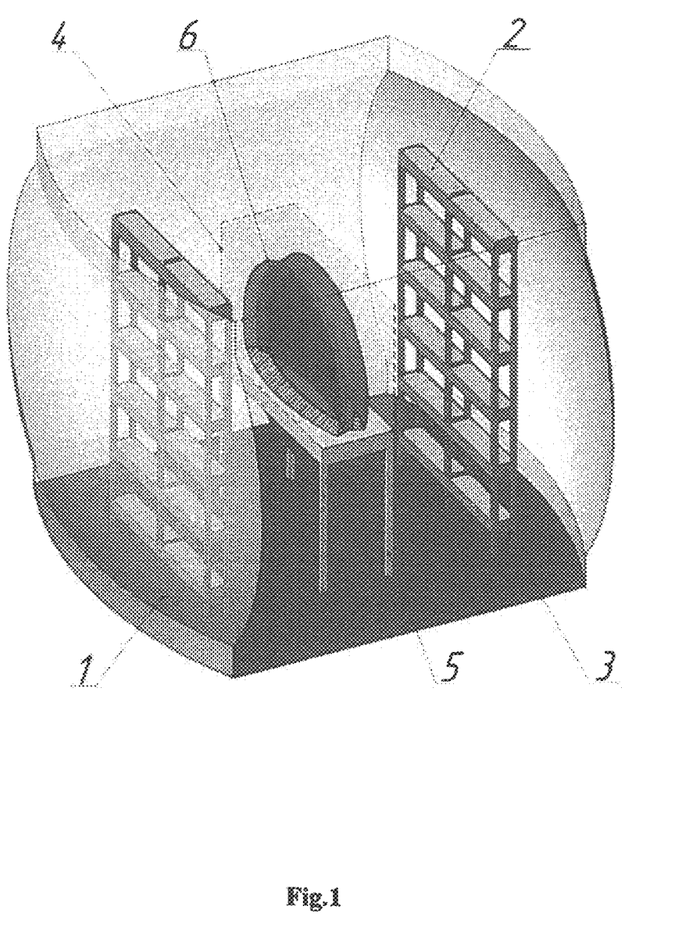
FIG. 1 is a three-dimensional view of the device having one pair of spherical reflectors and two distributed sources.
Figure 2:
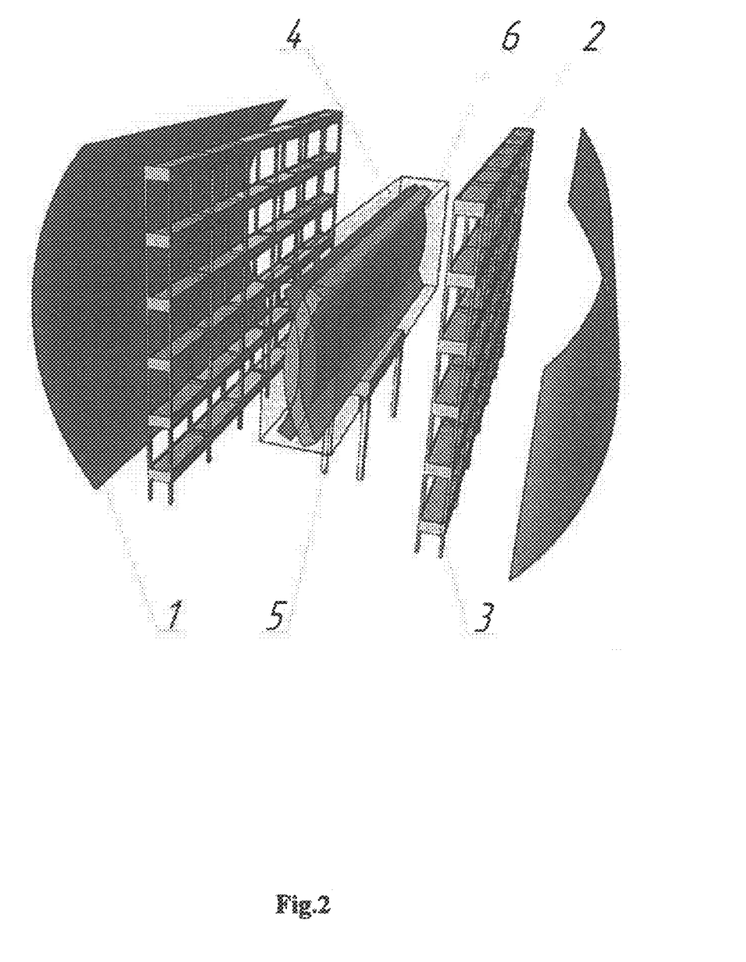
FIG. 2 is a three-dimensional view of the device having one pair of cylindrical reflectors and two distributed sources.
Figure 3:
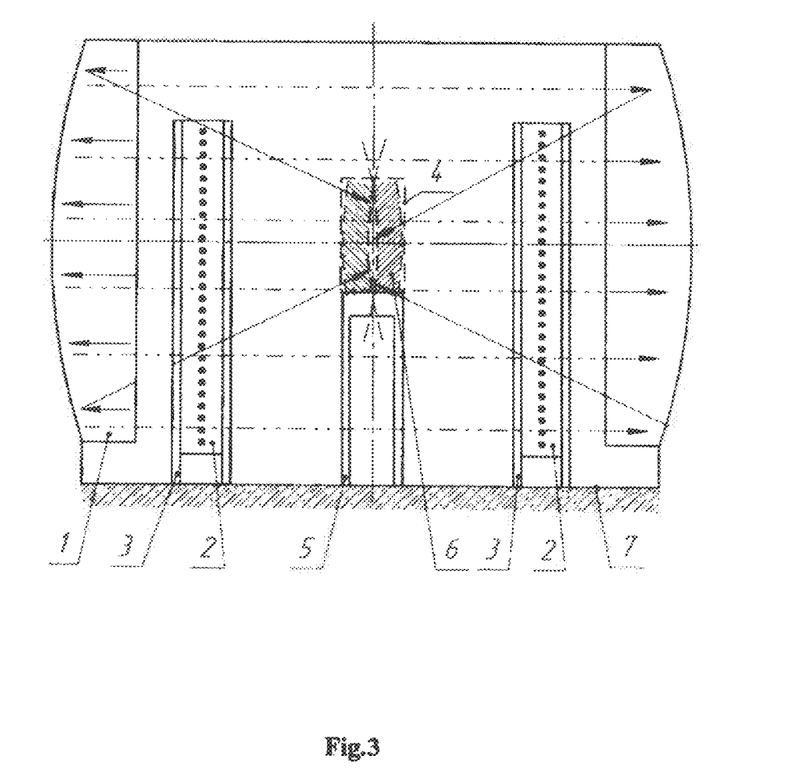
FIG. 3 is a sectional front view of the device having spherical or cylindrical reflectors.
Figure 4:
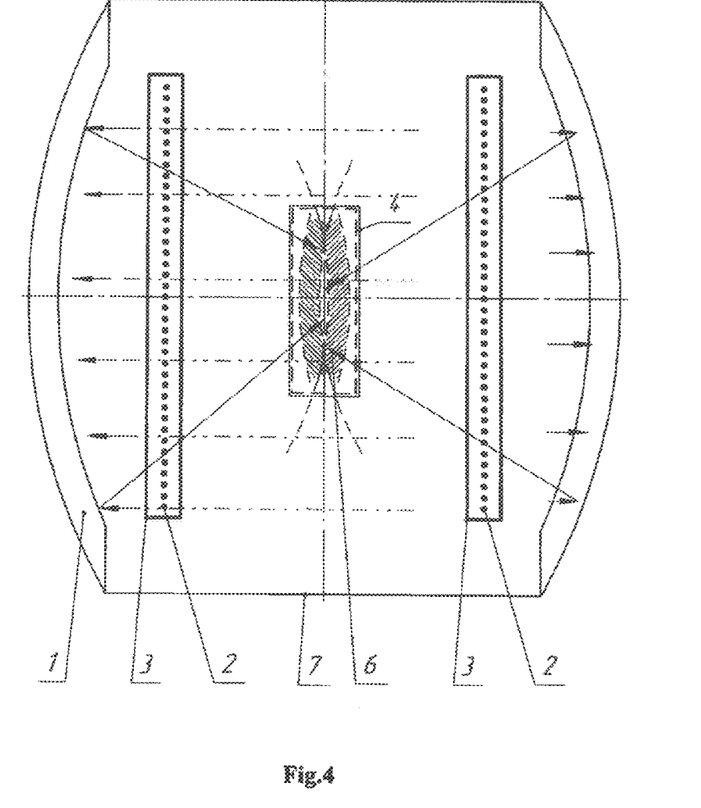
FIG. 4 is a sectional top view of the device having spherical reflectors.

The claimed multipurpose device for transmitting radiation from a distributed source to an object comprises two reflectors 1 coated with a material that reflects UV or IR beams well or, when UHF is used, made of copper or another nonmagnetic metal in the shape of truncated segments of a spherical or cylindrical surface. The reflectors are arranged opposite one another at a distance equal to between 0.6 to double the radius of the spherical or cylindrical surface. The focal areas of the spherical or cylindrical reflectors lie at a distance equal to half of their radius, and in this embodiment they are combined as two intersecting three-dimensional spheres or two three-dimensional cylinders 6. The means for positioning a radiation source 3, which may be designed, for example, as a stand having UV light-emitting diodes or solid-state UHF elements, or other radiation sources 2, arranged thereon, are provided in the aperture plane of either or both reflectors 1. An object 4 is positioned in the focal areas of reflectors 1. The assembled device is placed in a chamber 7. The spherical or cylindrical reflectors may serve as the walls of the chamber as shown in FIGS. 1, 2, and 3, or be used as separate reflectors located inside chamber 7.

Figure 5:
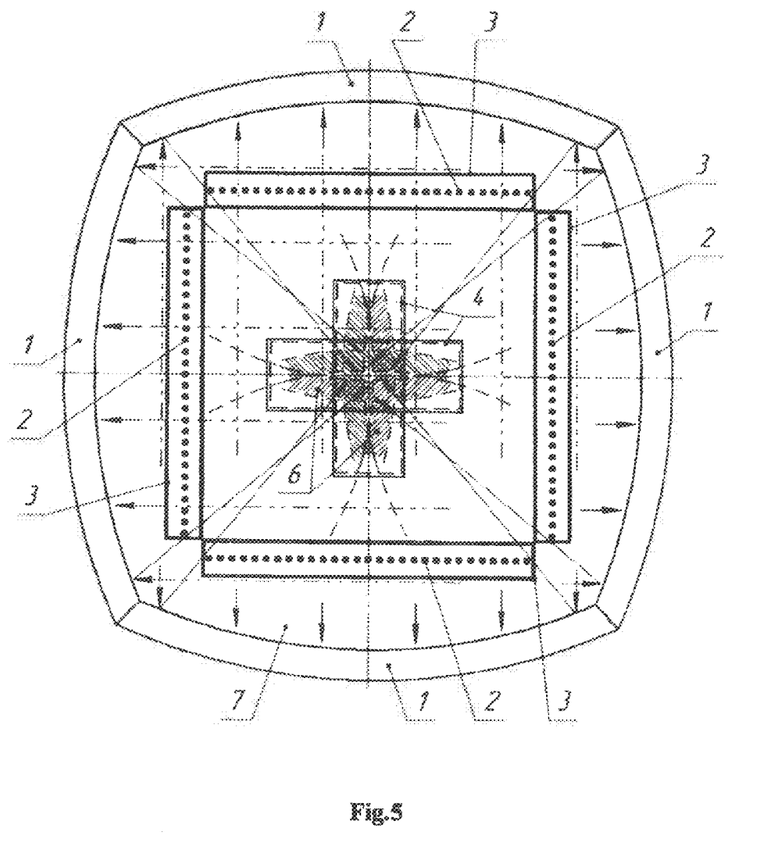
FIG. 5 is a sectional front view of the device having two pairs of spherical or cylindrical reflectors.

The device may further be provided with at least an additional pair of reflectors positioned opposite one another at a distance of 0.6 or double the radius of the spherical or cylindrical surface in a plane normal to the plane of the first pair of reflectors. In this embodiment, at least one further distributed radiation source is placed in the aperture of such further reflectors. This configuration produces a combined focal area in the shape of a three-dimensional cross. A third pair of reflectors may also be provided on top and at the bottom of the focal area of geometric shape similar to the one described above. One or two distributed radiation sources provided in the aperture of the top and bottom reflectors produce a three-dimensional combined focal area in the shape of three-coordinate cross.

The device operates as follows:

Object 4 is placed in focal area 5. One or two stands 3 provided with radiation sources 2 is/are placed in the aperture plane of either or both reflectors 1 in the chamber. Both reflectors in each pair reflect the radiation of sources 2 and concentrate it in focal areas 6, with object 4 placed therein.

When the claimed device is operated, it is reasonable to use reflectors having the radius of their spherical surface equal to 4 meters, a length of 4 meters, and a height of 2.5 meters to concentrate radiation, for example, UV radiation. It is reasonable to have a radiation source measuring 3 by 2 meters. All the elements of each distributed source transmit radiation to both reflectors.

Since the light-emitting diodes have a small geometrical size (3-5 mm in diameter), several thousand light-emitting diodes of this type arranged on a stand made of a UV-transparent material block a maximum of 2% of the light reflected from either of the reflectors. The additional optical losses of the system only total around 1%. Where UV or IR radiation is used, the object positioning means may be designed as a container made of a UV- or IR-transparent material, for example, quartz glass, or another. Where the distributed source is used in the UHF range, the stand and the object positioning means are to be made of radio-transparent materials.

Figure 6:
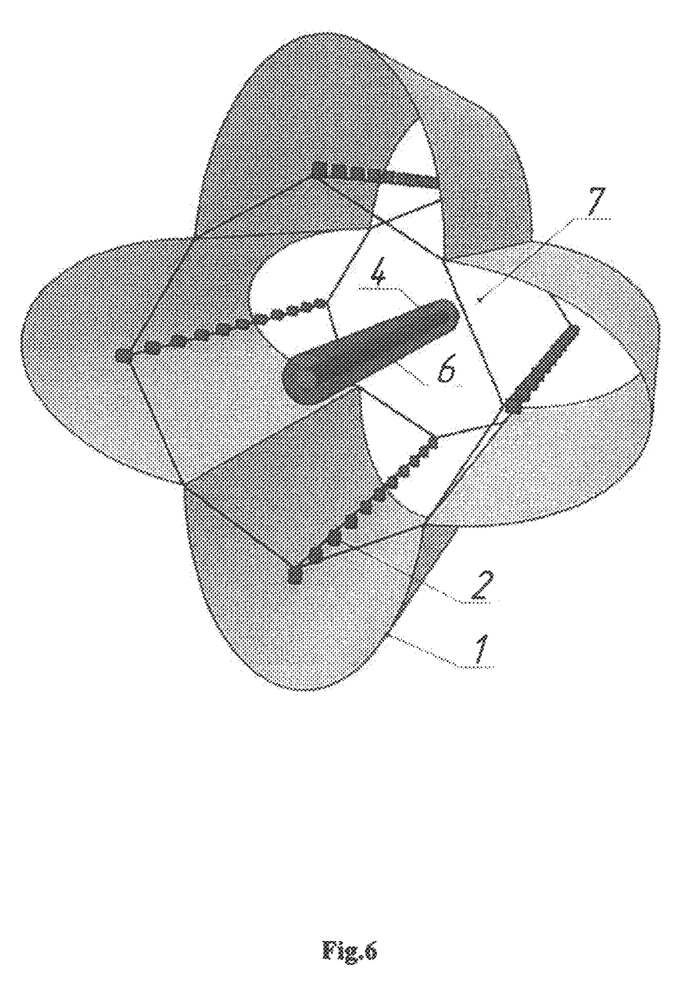
FIG. 6 is a diagrammatic view illustrating calculation of the focal length of a spherical reflector.
Figure 7:
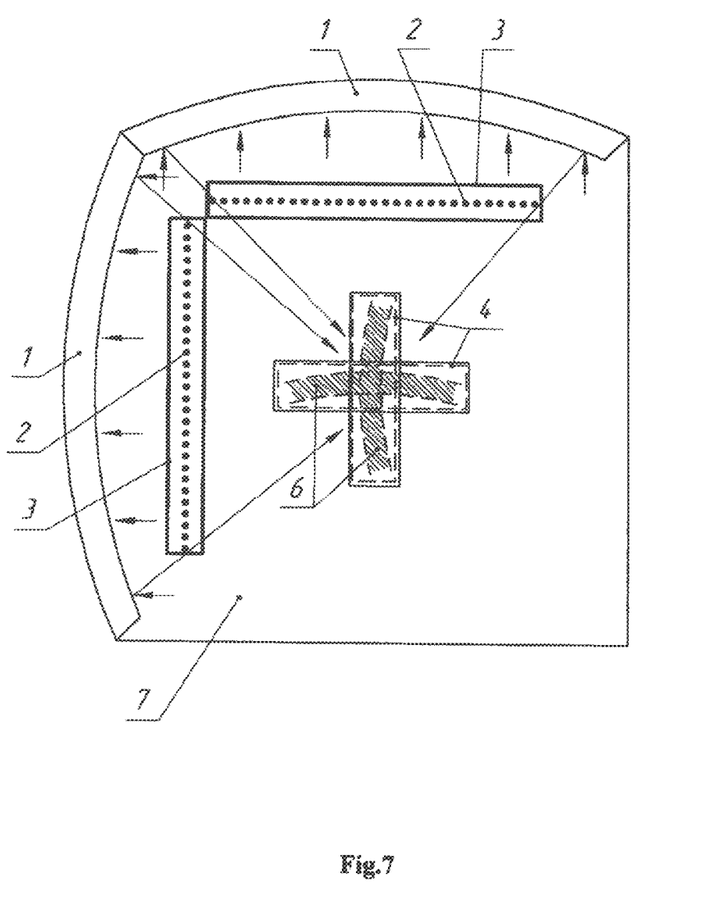
FIG. 7 is a sectional view of the device having a pair of spherical or cylindrical reflectors arranged at an angle to one another.
Figure 8:
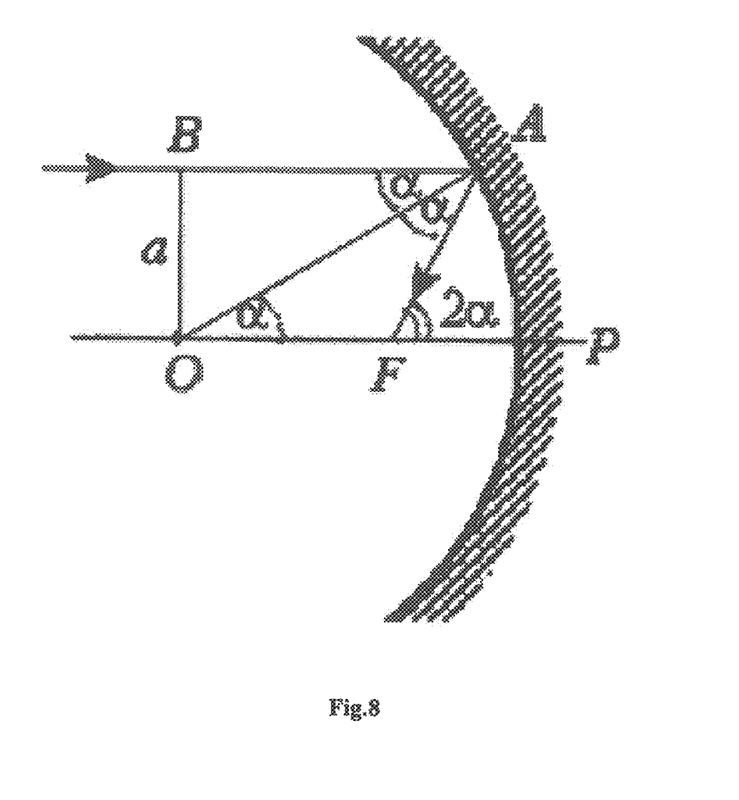
FIG. 8 is a diagram illustrating the calculation of the focal length of the spherical antenna.

FIG. 6 is a diagram illustrating calculation of the focal length FP of a concave spherical or cylindrical reflector of a radius R for a beam incident on the reflector in parallel with the main optical axis at a distance a therefrom. The geometrical configuration of the problem is clearly shown in the drawing. In an isosceles triangle AOF, the side OF can easily be described in terms of the base OA=R and its angle $\alpha$:

$$OF = \frac{R}{2\cos\alpha}.$$

The isosceles triangle OBA yields:

$$\cos\alpha = \frac{AB}{R} = \frac{\sqrt{R^2 - a^2}}{R}.$$

In which case $$OF = \frac{R^2}{2\sqrt{R^2 - a^2}}.$$

The desired focal length from the point F to the pole P:

$$FP = R - OF = R\left(1 - \frac{R}{2\sqrt{R^2 - a^2}}\right).$$

This is an equation for the focal area of a spherical or cylindrical reflector. The longer the distance a from the axis to the parallel beam the further the focus moves toward the reflector. For an reflector of a radius R=4 meters and a=0.5 meter, the focus shift is 1.5 cm, for a=1.0 meter, the focus shift is 7.5 cm, and for a=1.5 meters, it is 16 cm. The maximum distance a from the axis to the outermost parallel beam is 1.5 meters for the 3 meter long radiation source.

These calculations were made for only the principal optical axis. In a spherical or cylindrical surface, a multitude of principal optical axes may extend from the center to the surface within the limits of the effective angular aperture of the reflector.

Radiation emitted by all the elements of a source 3 meters long and 2 meters high to a section of a spherical reflector of the same length and height within the limits of its angular aperture in parallel with a multitude of optical axes can, therefore, produce a three-dimensional focal area beginning at a distance R/2 from the reflector and extending 16 cm toward the reflector. Radiation has the highest concentration at about R/2 from the reflector. Concentration does not take place at a distance of over 16 cm from R/2 toward the reflector. Two spheres arranged at a distance of, for example, the radius plus 4 cm use 12% of the additional volume of the combined focal area in which the concentration is high enough because concentrated radiation from both reflectors reaches this area for the concentration level of radiation to be distributed more evenly over the volume of the combined focal area.

Provided that the reflectors have the aforesaid dimensions and are arranged, for example, at a distance of the radius plus 4 cm, the effective combined focal area of both spherical reflectors measures 1.2×0.6×0.36 meters (compared to 1.2× 0.6×0.32 meters, or 12% smaller in volume, in the closest prior art device).

If a distributed source measuring 2 by 3 meters and consisting of a multitude of elements is placed in the spherical reflector aperture of the claimed device having reflectors 4 by 2.5 meters, 4 meter radius of the sphere or cylinder, and distance between the reflectors equal, for example, to the radius plus 4 cm, this large-volume source produces a smaller volume focal area of 1.2×0.6×0.36 meters. Each principal optical axis forms a focal line 16 cm long. The effective angular aperture of this reflector is equal to approximately 30 by 20 degrees. With principal optical axes examined at intervals of 1 degree, each reflector has at least 600 axes, or a total of 1,200 axes for both reflectors.

All the elements of the source transmit radiation to an reflector measuring 3 by 2 meters in parallel with each of the 1,200 principal optical axes. Radiation is concentrated at a high magnification ratio for each focal line 16 cm long, and the 1,200 focal lines produce a very efficient three-dimensional focal area 1.2×0.6×0.36 meters in size at a high magnification ratio at each point of its volume.

In the case of cylindrical reflectors 4 by 2.5 meters placed opposite one another at a distance of 4.04 meters, their combined focal area also measures 0.6 by 0.36 meters, and has a length of 4 meters.

With spherical or cylindrical reflectors 4 by 2.5 meters positioned at a distance of the radius minus 16 cm, the combined focal area has a thickness of 16 cm only, but an energy concentration twice as large as in the case of the reflectors positioned at a distance of the radius or slightly larger than the radius.

The device may have other dimensions as well, within the range of 0.05 meter to tens of meters, depending on the radius of the spherical or cylindrical surface.

With several thousand UV light-emitting diodes used in the device, its total power may reach several kilowatts. The device reduces power inputs several-fold because light-emitting diodes of identical radiation power are more economical than ordinary powerful lamps, and also lower power requirements, or increase significantly its throughput capacity as a result of radiation of a distributed source being concentrated by both reflectors within a relatively small combined three-dimensional focal area.

Metal filaments made of, for example, tungsten or carbon, may be used as a distributed source within the IR range. The filaments have a small thickness and are transparent enough to IR radiation reflected from the reflectors. Where a distributed gas burner consisting of fine tubing is used, the resulting distributed IR radiation source may be quite efficient, too. Vibrators may be used as a distributed source within the ultrasonic range.

Two reflectors in the shape of segments of a spherical or cylindrical surface arranged at a distance of 0.6 to twice the radius length, a distributed radiation source positioned in the aperture plane of either or both reflectors, and radiation transmitted to the combined focal area of both reflectors, with an object placed therein, enhance the reliability of the system many times over, reduce power requirements several-fold owing to economical light-emitting diodes used in the device, increase significantly the volume of the focal area or double the concentration level even though the area volume is decreased, distribute radiation concentration in the focal area more uniformly, and achieve a multiple increase in the device efficiency through concentration of radiation. One or two additional pairs of reflectors arranged in planes normal to the first pair of reflectors and distributed sources placed in the aperture plane of the additional reflectors produce a three-dimensional combined focal area of two or three pairs of reflectors achieving a very high energy concentration.

INDUSTRIAL APPLICABILITY

The claimed multipurpose device for concentrating radiation transmitted from a distributed source to an object positioned in a three-dimensional focal area may be used for irradiating liquids or gases pumped through the focal area, for example, for disinfecting water with UV radiation, heating running water, and other liquids and gases in the IR range, treating oil and gas products, and so on. The device may also be used for treating and disinfecting solid and free-flowing products, such as chemical fertilizers, seeds, and bulk food products. This multipurpose device can also be used for drying wood, UHF therapy, and the like. Liquids and gases may be treated in a flow-through system, bulk products may be treated in a system in which they pass slowly in a continuous flow through the focal area by gravity, and in the case of wood drying or UHF therapy, a quantity of wood or a patient is placed in the focal area for a certain time period. This multipurpose device can also be used in the ultrasonic range in systems for preparing uniform mixtures, cleaning, laundering, treatment of liquids, and in many other devices within any ranges of electromagnetic and sound waves.

What is claimed is:

1. A multipurpose device for transmitting radiation from a source to an object, comprising two reflectors each shaped as a truncated segment of a curved surface and both arranged to produce a combined focal zone, a distributed radiation source positioned in the aperture plane of at least one of the reflectors or in one of the focal areas of each reflector, and an object placed in the combined focal area of both reflectors.

2. A multipurpose device as claimed in claim 1, wherein the curved surface of each reflector is a spherical or cylindrical surface, and the distributed radiation source is placed in the aperture plane of at least one of the reflectors.

3. A multipurpose device as claimed in claim 1, wherein the reflectors are arranged opposite one another to produce a combined focal area.

4. A multipurpose device as claimed in claim 1, wherein the reflectors are arranged at an angle to one another to produce a combined focal area.

5. A multipurpose device as claimed in claim 1, further provided with at least one pair of spherical or cylindrical reflectors in a plane normal to the plane of the first pair of antenna reflectors.

6. A multipurpose device as claimed in claim 1, wherein the curved surface of the reflectors comprises at least a pair of elliptical cylinders positioned opposite one another to produce a single combined focal area for an object to be placed therein, distributed sources being arranged in the two other focal areas.

7. A multipurpose device as claimed in claim 5, wherein one elliptical reflector only is used in at least two planes, one distributed source being placed in the focal area of each reflector, and an object being placed in the combined focal area of said reflectors.

* * * * *